US00PP11949P2

(12) United States Plant Patent
Booman

(10) Patent No.: US PP11,949 P2
(45) Date of Patent: Jun. 19, 2001

(54) BEGONIA PLANT NAMED 'ATLANTA JAZZ'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,776

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Atlanta Jazz', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Atlanta Jazz'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, salt tolerance and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar, 'Atlanta Jazz', has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Atlanta Jazz'. These characteristics in combination distinguish 'Atlanta Jazz' as a new and distinct Rex Begonia:

1. Uniform growth habit.

1. Moderate plant vigor.

3. Does not require winter dormancy.

4. Interesting and attractive leaf coloration and pattern.

In side-by-side comparisons conducted by the Inventor in Vista, Calif., plants of the new Rex Begonia differ from plants of the nonpatented cultivar 'Merry Christmas Corkscrew' in the following characteristics:

1. Plants of the new Rex Begonia are more vigorous and are denser than plants of the cultivar 'Merry Christmas Corkscrew'.

2. Leaves of plants of the new Rex Begonia and the cultivar 'Merry Christmas Corkscrew' differ in coloration and pattern.

3. Leaves of plants of the new Rex Begonia do not have a "corkscrew" formation whereas leaves of plants of the cultivar 'Merry Christmas Corkscrew' have a "corkscrew" formation.

4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium' in the following characteristics:

1. Plants of the new Rex Begonia are more compact and denser than plants of the cultivar 'Lillium'.

2. Plants of the new Rex Begonia have flatter and more rounded leaves than plants of the cultivar 'Lillium'.

3. Leaves of plants of the new Rex Begonia and the cultivar 'Lillium' differ in coloration and pattern.

4. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a side perspective view of a typical plant of 'Atlanta Jazz'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar, 'Atlanta Jazz'.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength.

*Vigor.*—Moderate.

*Plant height, soil surface to top of leaf canopy.*—About 29.5 cm.

*Plant width.*—About 58 cm.

*Leaves.*—Arrangement: Simple. Length: Petiole to apex: About 18 cm. Base to apex: About 23.3 cm. Width: About 14.2 cm. Shape: Oblique, somewhat elliptic. Apex: Acute. Base: Asymmetrically cordate. Margin: Pectinate; young leaves, almost serrate; irregularly undulate. Texture: Leathery, rugose; pubescence on lower surface veins. Color: Young foliage, upper surface: Margin: 200A. Central venal areas: 200C with overtones of dark green, 147A, 185A "bleeding through". Blade: Interveinal areas of close to iridescent 194C; background of 146A extending to margin. Young foliage, lower surface: Margin: 183D. Central venal areas: 183D. Background: 147D. Mature, fully expanded, foliage, upper surface: Margin: Dark brown, 200A, but close to 202A. Central venal areas: Outlined by velvety 200A. Blade: Splotches of metallic 185C to 185D becoming iridescent 194C. Background: Close to 147A extending to margin. Veins: Main veins very marked, outlined by 200A to 202B then becoming 147A. Mature, fully expanded, foliage, lower surface: Margin: Darker than 183A. Blade: 183A, shading to 183C along veins. Background: 148D. Veins: Darker than 183A; reticulate.

*Petioles.*—Length: About 19.4 cm. Diameter: About 7.5 mm. Shape: Longitudinally grooved. Texture: Pubescent. Color: 178A.

*Stipules.*—Length: About 13.5 mm. Diameter at base: About 5 mm. Shape: Subulate, ensiform, deltoid. Color: 180A.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 3.6 cm. Depth (height): About 2.2 cm. Aspect: Drooping about 40° from vertical. Fragrance: None.

*Flower buds.*—Shape: Spherical; bulbous with marginal lip. Length: About 9.5 mm. Diameter: About 7 mm. Color: 50A to 52B.

*Tepals.*—Arrangement: Rosette. Length: About 1.7 cm. Width: About 1 cm. Shape: Ovate with obtuse apex. Margin: Entire. Texture: Smooth, waxy; iridescent, translucent. Color: When opening, upper surface: 55B to 51B. When opening to lower surface: 55B to 50A to 50B. Fully opened, upper surface: 50B towards center, 50C towards margin. Fully opened, lower surface: 50A towards center, 55B towards margin.

*Peduncles.*—Angle: About 30° from vertical. Length: About 7 cm. Diameter: About 1.5 mm. Strength: Firm. Texture: Smooth, waxy. Color: 45C.

*Pedicels.*—Angle: About 30° from vertical. Length: About 1.7 cm. Diameter: About 1 mm. Strength: Flexible, moderately weak. Texture: Smooth, waxy. Color: 45C.

*Reproductive organs.*—Male flowers: Stamen quantity: About 112, globose mass. Anther shape: Rhomboidal; lower sides curved inwardly. Anther length: About 2 mm. Filament length: About 1 mm. Anther color: 16B. Filament color: 50D. Pollen: Not observed. Female flowers: Pistil length: About 2.1 cm. Stigma shape: Funnel; bilobate. Stigma color: 168A. Ovary: Inferior; three-winged; one large top wing and two lower wings, both surfaces, 50A to 50B.

Disease resistance: Resistance to diseases common to Rex Begonia has not been determined.

Seed production: Seed production has not been observed.

It is claimed:

1. A new and distinct cultivar of Rex Begonia plant named 'Atlanta Jazz', as illustrated and described.

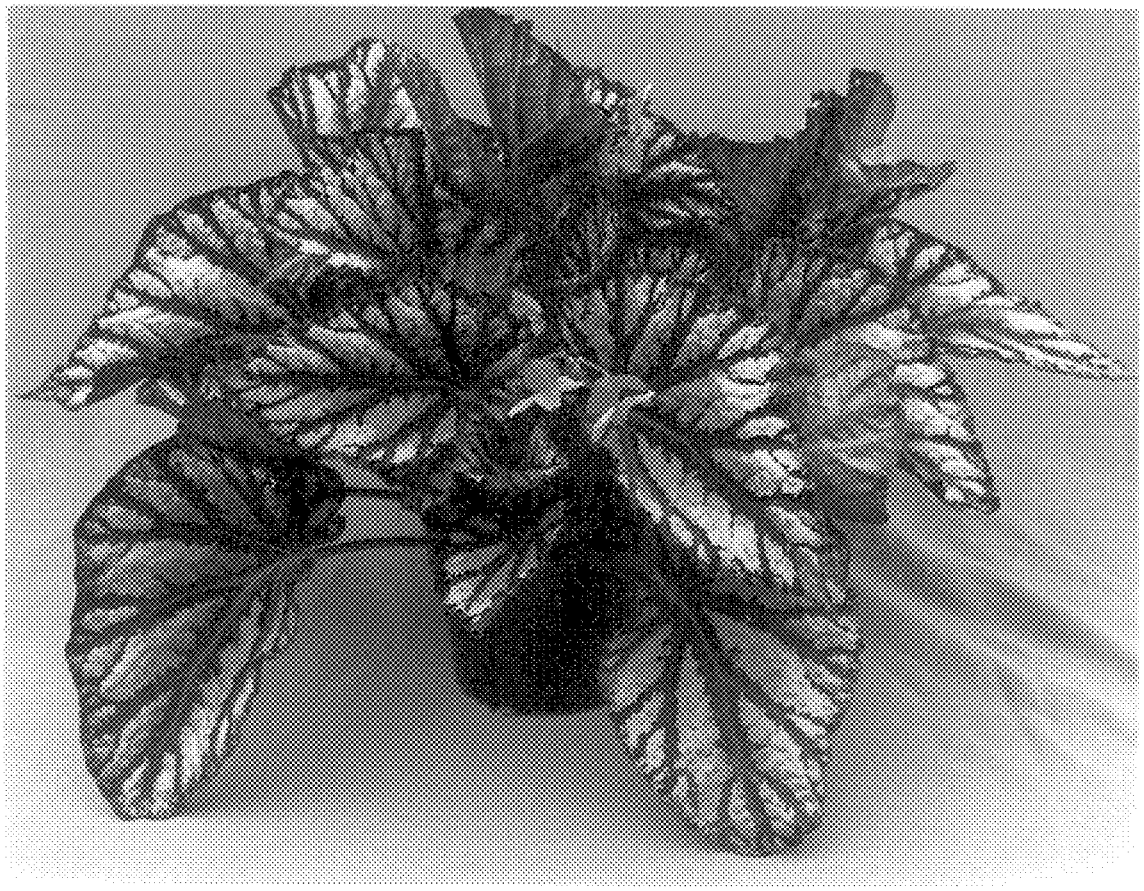

* * * * *